(12) United States Patent
Sano et al.

(10) Patent No.: US 7,821,645 B2
(45) Date of Patent: Oct. 26, 2010

(54) MICROSTRUCTURAL FEATURE AND MATERIAL PROPERTY MONITORING DEVICE FOR METALLIC MATERIAL

(75) Inventors: Mitsuhiko Sano, Tokyo (JP); Kazuhiro Ohara, Tokyo (JP)

(73) Assignee: Toshiba Mitsubishi-Electric Industrial Systems Corporation, Tokyo (JP)

( * ) Notice: Subject to any disclaimer, the term of this patent is extended or adjusted under 35 U.S.C. 154(b) by 517 days.

(21) Appl. No.: 11/994,666

(22) PCT Filed: Jan. 11, 2007

(86) PCT No.: PCT/JP2007/050215
§ 371 (c)(1), (2), (4) Date: Jan. 4, 2008

(87) PCT Pub. No.: WO2008/084538
PCT Pub. Date: Jul. 17, 2008

(65) Prior Publication Data
US 2010/0128281 A1    May 27, 2010

(51) Int. Cl.
G01B 11/02    (2006.01)
(52) U.S. Cl. .................................... 356/502
(58) Field of Classification Search .............. 356/502
See application file for complete search history.

(56) References Cited

U.S. PATENT DOCUMENTS 5,824,908 A * 10/1998 Schindel et al. ............ 73/632
6,628,404 B1 * 9/2003 Kelley et al. ............. 356/502

FOREIGN PATENT DOCUMENTS

| GB | 2 172 106 A | 9/1986 |
|---|---|---|
| JP | 53-126991 | 11/1978 |
| JP | 56-58659 | 5/1981 |
| JP | 7-20095 | 1/1995 |
| JP | 2000-146923 | 5/2000 |
| JP | 2002-213936 | 7/2002 |
| JP | 2003-329652 | 11/2003 |
| JP | 2004-333169 | 11/2004 |
| WO | WO 02/103347 A2 | 12/2002 |

* cited by examiner

*Primary Examiner*—Tarifur Chowdhury
*Assistant Examiner*—Jonathon D Cook
(74) *Attorney, Agent, or Firm*—Leydig, Voit & Mayer, Ltd.

(57) ABSTRACT

A microstructural feature and material property monitoring device for a metallic material that can easily adjust relative position between an irradiation position of laser beams applied to the metallic material to propagate pulsed ultrasonic waves in the metallic material and detection position of a laser interferometer, and therefore can accurately monitor the microstructural feature and material property of the metallic material. The device relatively moves the irradiation position of the laser beams generated by a laser oscillator and the detection position of the laser interferometer. The irradiation position of the laser beams generated from a laser oscillator and the detection position of the laser interferometer are controlled to be aligned with a relative position according to the microstructural feature and material property of the metallic material based on the time from the transmission of the pulsed ultrasonic waves to the detection by the laser interferometer. After the alignment, the microstructural feature and material property of the metallic material is calculated based on the waveform of the pulsed ultrasonic waves generated as an electrical signal by the laser interferometer.

5 Claims, 7 Drawing Sheets

OSCILLATION INTENSITY DISTRIBUTION OF LONGITUDINAL WAVE

OSCILLATION INTENSITY DISTRIBUTION OF TRANSVERSE WAVE

IN THE CASE WHERE TRANSMISSION SURFACE AND RECEPTION SURFACE ARE OPPOSITE SURFACES

IN THE CASE WHERE TRANSMISSION SURFACE AND RECEPTION SURFACE ARE SAME SURFACE

MICROSTRUCTURAL FEATURE AND MATERIAL PROPERTY MONITORING DEVICE FOR METALLIC MATERIAL

TECHNICAL FIELD

The present invention relates to a microstructural feature and material property monitoring device for monitoring the microstructural feature and material property of a metallic material.

BACKGROUND ART

In recent years, various attempts have been made to separately create the microstructural feature and material property of a metallic material according to the application of metallic material. For example, a method has begun to be used in which, when a metallic material is cooled after hot rolling, cooling water is sprayed at a high pressure in large quantities to increase the cooling rate of steel plate, by which the metallographic structure is changed to provide desired tensile strength or ductility. Conventionally, however, in practically using such a manufacturing method, there has been unavailable a method for efficiently checking whether or not the manufactured metallic material has the required microstructural feature and material property.

Conventionally, the mechanical properties such as tensile strength, ductility, and formability of a metallic material have been measured by a destructive test such as a tensile test. However, such a measuring method requires several hours to several days before the test result is obtained, and also has a problem in that 100% test cannot be performed because of destructive test. Therefore, it has been strongly demanded that the microstructural feature and material property of a metallic material be tested in a non-destructive mode.

To cope with the above problems, as one method for testing the microstructural feature and material property of a metallic material in a non-destructive mode, there has been known a method in which ultrasonic waves are transmitted into a metallic material, for example, a metal piece, and the microstructural feature and material property of a metallic material are monitored based on the propagation characteristics of the ultrasonic waves. With this method, various characteristic values of microstructural feature and material property can be monitored by utilizing any of the oscillation modes of ultrasonic waves. For example, from the attenuation characteristics of the high-frequency component of longitudinal wave, the crystal grain size of metal piece can be detected, and further the measurement values of yield stress and tensile stress, which correlate strongly with the crystal grain size, can be obtained. Also, from the propagation velocity of transverse wave, the modulus of elasticity of metal piece can be detected, and further from the anisotropy of the modulus of elasticity, the measurement value of Lankford value (r value), which is one of the characteristic values of microstructural feature and material property representing the formability of metal piece, can be obtained.

In monitoring the microstructural feature and material property of the metal piece (metallic material) by the above-described method, as means for transmitting ultrasonic waves into the metal piece and means for receiving ultrasonic waves having propagated in the metal piece, for example, a method has been widely known in which a piezoelectric element is brought into contact with the metal piece. In this method, however, the piezoelectric element must be brought into close contact with the metal piece via a liquid etc., so that there arise a problem in that this method is unsuitable for on-line measurement especially on a production line and a problem in that this method is unsuitable for the measurement of crystal grain size because the oscillation frequency is low (<1 MHz).

On the other hand, in recent years, a method has been used in which pulse-shaped ultrasonic waves are transmitted into the metal piece by applying pulse laser beams to the surface of metal piece (for example, refer to Patent Document 1). This method has an advantage that the ultrasonic waves can be transmitted into the metal piece, for example, by applying pulse laser beams from a position separate from the metal piece and an advantage that the pulse ultrasonic waves containing a high-frequency component of several tens megahertz or higher can be transmitted into the metal piece, for example, by decreasing the pulse width of laser beams.

Also, in recent years, a method has been used in which the ultrasonic waves having propagated in the metal piece is received by utilizing a laser interferometer. In this method, by applying laser beams to the metal piece separately from the laser beams for transmitting ultrasonic waves, minute ultrasonic wave oscillations appearing on the surface of metal piece are read by causing the reflected light to interfere with the reference light. Therefore, this method has an advantage that the minute ultrasonic wave oscillations appearing on the surface of metal piece can be received, for example, from a position separate from the metal piece and an advantage that ultrasonic wave oscillations of high frequency of several tens megahertz or higher can be received.

Patent Document 1: Japanese Patent Publication No. 61-54179

DISCLOSURE OF THE INVENTION

Problems to be Solved by the Invention

The pulse ultrasonic waves transmitted into the metal piece by applying the pulse-shaped laser beams have a strong directivity depending on the oscillation mode. FIG. 7 is diagrams showing the directivity of the pulse ultrasonic waves transmitted into the metal piece, FIG. 7a being a diagram showing the oscillation intensity distribution of longitudinal wave, and FIG. 7b being a diagram showing the oscillation intensity distribution of transverse wave. As shown in FIGS. 7a and 7b, when laser beams are applied perpendicularly to one surface of metal piece, the longitudinal wave has a strong directivity in the direction perpendicular to one surface of the metal piece irradiated with the laser beams. Also, the transverse wave has a strong directivity in the direction of about 45 degrees with respect to one surface of the metal piece.

Therefore, in the case where the pulse ultrasonic waves having propagated in the metal piece is received by the laser interferometer, according to the oscillation mode of pulse ultrasonic waves to be detected, the optimal receiving position, that is, the position irradiated with the laser beams for reception exists. For example, in the case where laser beams are applied to one surface (hereinafter referred also to as a "ultrasonic wave transmitting surface") of metal piece by using laser beams having a minute irradiation region for transmission, for the longitudinal wave, a position at which the vertical line from the ultrasonic wave transmitting surface intersects with the other surface (hereinafter referred also to as a "ultrasonic wave receiving surface") on the reverse side with respect to the one surface of metal piece is the optimal receiving position, and for the transverse wave, a position at which the straight line making 45 degrees with respect to the vertical line from the ultrasonic wave transmitting surface intersects with the ultrasonic wave receiving surface is the optimal receiving position. By applying laser beams for reception to the optimal receiving position, a strong signal intensity can be obtained.

That is to say, if the position irradiated with the laser beams for reception (the detection position of laser interferometer) can be aligned accurately with the optimal receiving position, only the ultrasonic waves of a necessary oscillation mode can be received properly, and the measurement error can be decreased without being affected by ultrasonic wave oscillations of other oscillation modes and various turbulence noise. However, in the conventional method including one described in Patent Document 1, the positional relationship between the position to which laser beams for transmission are applied and the position to which laser beams for reception are applied is adjusted manually, so that there arises an inevitable problem in that the measurement accuracy varies according to the skill of a person who makes adjustment.

The present invention has been made to solve the above problems, and accordingly an object thereof is to provide a microstructural feature and material property monitoring device for a metallic material, which can easily adjust the relative position between the irradiation position of laser beams applied to the metallic material to propagate pulse ultrasonic waves into the metallic material and the detection position of a laser interferometer, and therefore can accurately monitor the microstructural feature and material property of the metallic material.

Means for Solving the Problems

A microstructural feature and material property monitoring device for metallic material of the present invention is a microstructural feature and material property monitoring device for a metallic material, which monitors the microstructural feature and material property of a metallic material, comprises a laser oscillator which applies laser beams to a first surface of the metallic material and transmits pulse ultrasonic waves into the metallic material, a laser interferometer which detects the pulse ultrasonic waves having propagated in the metallic material on a second surface on the side opposite to the first surface of the metallic material and sends the pulse ultrasonic waves as an electrical signal, moving means which is configured so as to be capable of relatively moving the irradiation position of the laser beams generated from the laser oscillator and the detection position of the laser interferometer, control means which aligns the irradiation position of the laser beams generated from the laser oscillator and the detection position of the laser interferometer with a relative position according to the microstructural feature and material property of the metallic material to be monitored by controlling the moving means based on the time from the transmission of the pulse ultrasonic waves to the detection carried out by the laser interferometer, and calculating means which calculates the microstructural feature and material property of the metallic material based on the waveform of the pulse ultrasonic waves generated as an electrical signal by the laser interferometer.

Effect of the Invention

According to the present invention, the microstructural feature and material property monitoring device for a metallic material, which monitors the microstructural feature and material property of the metallic material, includes a laser oscillator which applies laser beams to a first surface of the metallic material and transmits pulse ultrasonic waves into the metallic material, a laser interferometer which detects the pulse ultrasonic waves having propagated in the metallic material on a second surface on the side opposite to the first surface of the metallic material and sends the pulse ultrasonic waves as an electrical signal, moving means which is configured so as to be capable of relatively moving the irradiation position of the laser beams generated from the laser oscillator and the detection position of the laser interferometer, control means which aligns the irradiation position of the laser beams generated from the laser oscillator and the detection position of the laser interferometer with a relative position according to the microstructural feature and material property of the metallic material to be monitored by controlling the moving means based on the time from the transmission of the pulse ultrasonic waves to the detection carried out by the laser interferometer, and calculating means which calculates the microstructural feature and material property of the metallic material based on the waveform of the pulse ultrasonic waves generated as an electrical signal by the laser interferometer. Thereby, the relative position between the irradiation position of the laser beams applied to the metallic material to propagate pulse ultrasonic waves into the metallic material and the detection position of the laser interferometer can be adjusted easily, so that the microstructural feature and material property of the metallic material can be monitored accurately.

DESCRIPTION OF SYMBOLS

Figure 1:
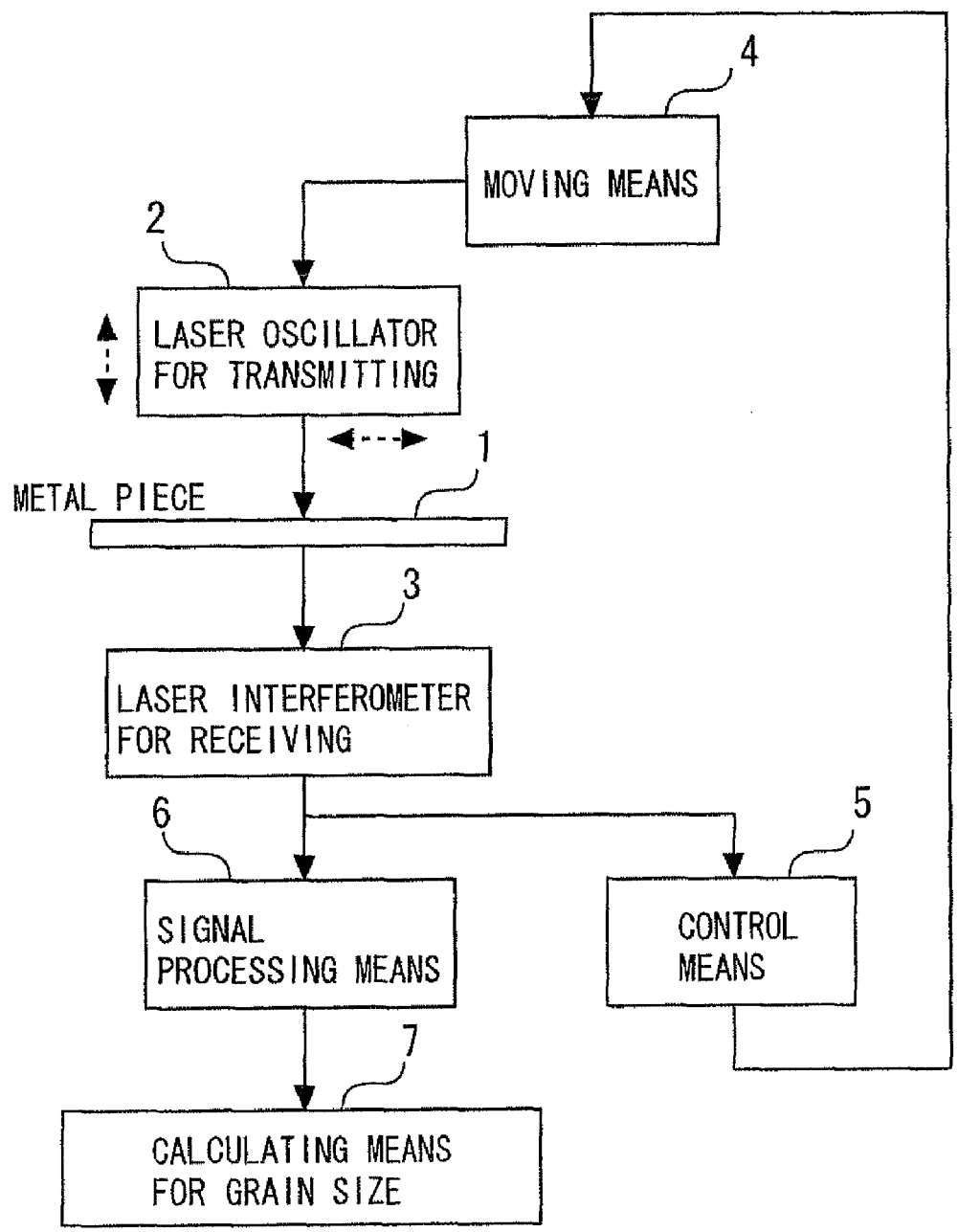
FIG. 1 is a block diagram showing the configuration of a microstructural feature and material property monitoring device for a metallic material in accordance with a first embodiment of the present invention.

| 1 metal piece, | 2 laser oscillator, | 3 laser interferometer, |
|---|---|---|
| 4 moving means, | 5 control means, | 6 signal processing means, |
| 7 calculating means, | 8 longitudinal wave echo extracting means, | |

-continued 9 frequency analyzing means,
10 identifying means for attenuation curve of each frequency,
11 multi-order function fitting means

BEST MODE FOR CARRYING OUT THE INVENTION

First, before the specific embodiment of the present invention is explained, as a method for measuring a crystal grain size in a non-destructive mode, a method for utilizing the attenuation of ultrasonic waves generated by the scattering of crystal grains is explained.

The ultrasonic waves have various oscillation modes, in the grain size measuring method for utilizing the scattering of crystal grains, a longitudinal wave of the aforementioned vibration modes is utilized. The attenuation of longitudinal wave is expressed by the following formula using an attenuation constant a.

[Formula 1]

$$p = p_0 \cdot \exp(-a \cdot x) \quad (1)$$

in which, p and $p_0$ are sound pressures, and x is a propagation distance in a steel plate.

Also, in the case where the frequency of longitudinal wave is in the "Raileigh region", the attenuation constant a is expressed by the following formula.

[Formula 2]

$$a = a_1 \cdot f + a_4 \cdot f^4 \quad (2)$$

in which, $a_1$ and $a_4$ are coefficients, and f is a longitudinal wave frequency. As described above, the attenuation constant a is approximated by the quartic function of the longitudinal wave frequency f. Also, the first term of Formula (2) indicates an absorption attenuation term caused by internal friction, and the second term thereof indicates a Raileigh scattering term. The aforementioned term "Raileigh region" means a region in which the crystal grain size is far smaller than the wavelength of longitudinal wave, and is a range, for example, meeting the condition of the following formula.

[Formula 3]

$$0.03 < d/\lambda < 0.3 \quad (3)$$

in which, d is a crystal grain size, and $\lambda$ is the wavelength of longitudinal wave.

Also, it is known that the quartic coefficient $a_4$ in Formula (2) satisfies the following formula.

[Formula 4]

$$a_4 = S \cdot d^3 \quad (4)$$

in which, S is a scattering constant. That is to say, the coefficient $a_4$ is proportional to the cube of the crystal grain size d.

The longitudinal wave transmitted by a transmitter contains frequency components having a certain distribution in the waveform thereof, so that the attenuation factor of each of the frequency components can be obtained by frequency-analyzing the received waveform. Further, the propagation distance in the steel plate is found by detecting the time difference between transmission and reception, so that the coefficients in Formula (2) can be derived based on the attenuation factor of each frequency component and the propagation distance. By determining the scatter constant S in advance using a standard sample etc., the crystal grain size d can be obtained by Formula (4).

Next, a microstructural feature and material property monitoring device for a metallic material in accordance with the present invention will be described in detail with reference to the accompanying drawings. In the drawings, the same reference numerals are applied to the same or equivalent elements, and the duplicated explanation thereof is simplified or omitted as needed.

First Embodiment

Figure 2:
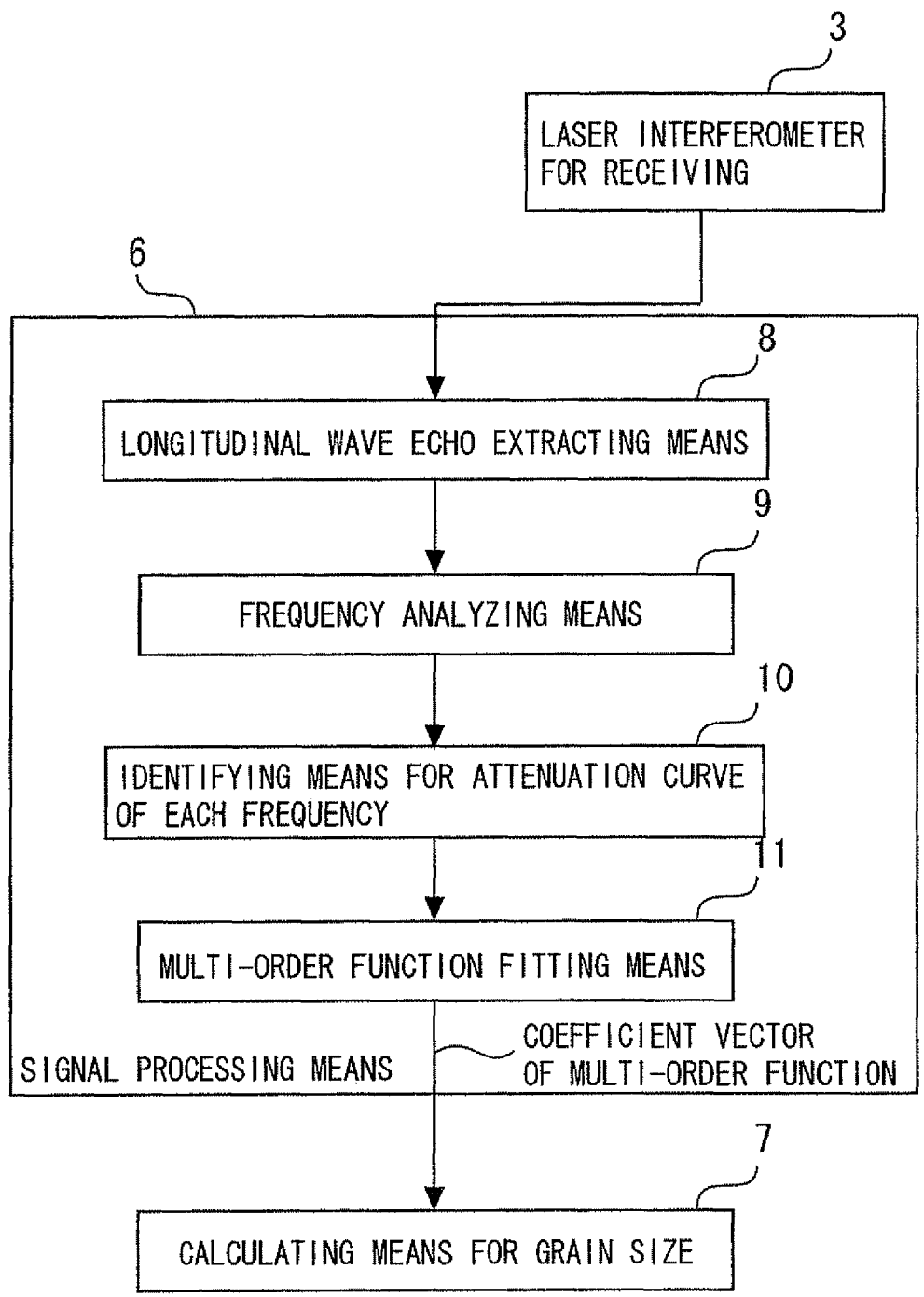
FIG. 2 is a block diagram showing the configuration of an essential portion of the microstructural feature and material property monitoring device for a metallic material in accordance with a first embodiment of the present invention.

FIG. 1 is a block diagram showing the configuration of a microstructural feature and material property monitoring device for a metallic material in accordance with a first embodiment of the present invention, and FIG. 2 is a block diagram showing the configuration of an essential portion of the microstructural feature and material property monitoring device for a metallic material in accordance with a first embodiment of the present invention.

In FIG. 1, reference numeral 1 denotes a plate-shaped metal piece (metallic material) consisting of a material to be monitored, reference numeral 2 denotes a laser oscillator for transmitting pulse ultrasonic waves, which is provided above the metal piece 1 to apply pulse laser beams to the top surface of the metal piece 1 and transmit pulse ultrasonic waves into the metal piece 1. And reference numeral 3 denotes a laser interferometer for receiving pulse ultrasonic waves generated as an electrical signal, which is provided under the metal piece 1 to detect the pulse ultrasonic waves, having propagated in the metal piece 1, on the bottom surface of the metal piece 1 by applying laser beams separate from the aforementioned ones for transmission to the bottom surface of the metal piece 1. The laser oscillator 2 or the laser interferometer 3 may be configured so that the body (light source) thereof is located at a position separate from the metal piece 1, and an optical fiber is laid from the body to above or below the metal piece 1.

Reference numeral 4 denotes moving means capable of relatively moving the irradiation position on the metal piece 1 of the pulse laser beams generated from the laser oscillator 2 and the detection position on the metal piece 1 at which the pulse ultrasonic waves are detected by the laser interferometer 3. Reference numeral 5 denotes control means that aligns the irradiation position on the metal piece 1 of the pulse laser beams generated from the laser oscillator 2 and the detection position on the metal piece 1 at which the pulse ultrasonic waves are detected by the laser interferometer 3 with the relative position in accordance with the microstructural feature and material property of the metal piece 1 to be monitored by controlling the moving means 4 based on the time from the transmission of pulse ultrasonic waves to the detection carried out by the laser interferometer 3. Reference numeral 6 denotes signal processing means that receives a detection signal sent from the laser interferometer 3 and processes the received detection signal to calculate the microstructural feature and material property of the metal piece 1, and reference numeral 7 denotes calculating means for calculating the microstructural feature and material property of the metal piece 1 based on the processing result of the signal processing means 6, that is, the waveform of the pulse ultrasonic waves generated as an electrical signal by the laser interferometer 3. As one example of the calculating means 7, grain size calculating means for calculating the crystal grain size of the metal piece 1 is shown.

As the laser oscillator 2 for transmitting pulse ultrasonic waves, for example, a YAG (yttrium-aluminum-garnet) laser, which can perform Q switch operation and can generate laser beams with high energy and short pulse, is suitable. In the case where the YAG laser is employed as the laser oscillator 2, the pulse width of laser beams is about several nanoseconds to ten plus several nanoseconds. The laser beams generated from the laser oscillator 2 is made to have the aimed beam diameter, for example, by being focused by a lens, and thereafter are applied to the top surface of the metal piece 1, which is a material to be monitored. When the laser beams generated from the laser oscillator 2 are applied to the surface of the metal piece 1, pulse ultrasonic waves are excited in the metal piece 1. The pulse width of the pulse ultrasonic waves excited in the metal piece 1 is several times the pulse width of the pulse laser beams generated from the laser oscillator 2.

Also, the laser interferometer 3 applies laser beams for reception that are separate from the laser beams for transmission to the bottom surface of the metal piece 1, which is directed to the side reverse to the top surface thereof to which the pulse laser beams for transmission is applied, and causes the reflected light thereof to interfere with the reference light to detect the light and darkness of interference fringe by using a photodetector, by which the waveform of minute oscillation at the time when the pulse ultrasonic waves appear on the bottom surface of the metal piece 1 is delivered as an electrical signal. Although various types of laser interferometers 3 have been proposed, in the case where the surface of the metal piece 1 is rough, a Fabry-Perot interferometer or an interferometer of two-wave mixing type using a photorefractive element is suitable. The signal processing means 6 carries out various processing necessary for calculating the microstructural feature and material property of the metal piece 1 based on the waveform of pulse ultrasonic waves generated as an electrical signal by the laser interferometer 3, and, for example, makes the grain size calculating means 7 calculate the crystal grain size of the metal piece 1.

Next, the processing operation of the signal processing means 6 and the calculating operation of the grain size calculating means 7 are explained in detail with reference to FIG. 2. In FIG. 2, the signal processing means 6 is made up of, for example, storage means (not shown), longitudinal wave echo extracting means 8, frequency analyzing means 9, identifying means 10 for attenuation curve of each frequency, and multi-order function fitting means 11.

Figure 3:
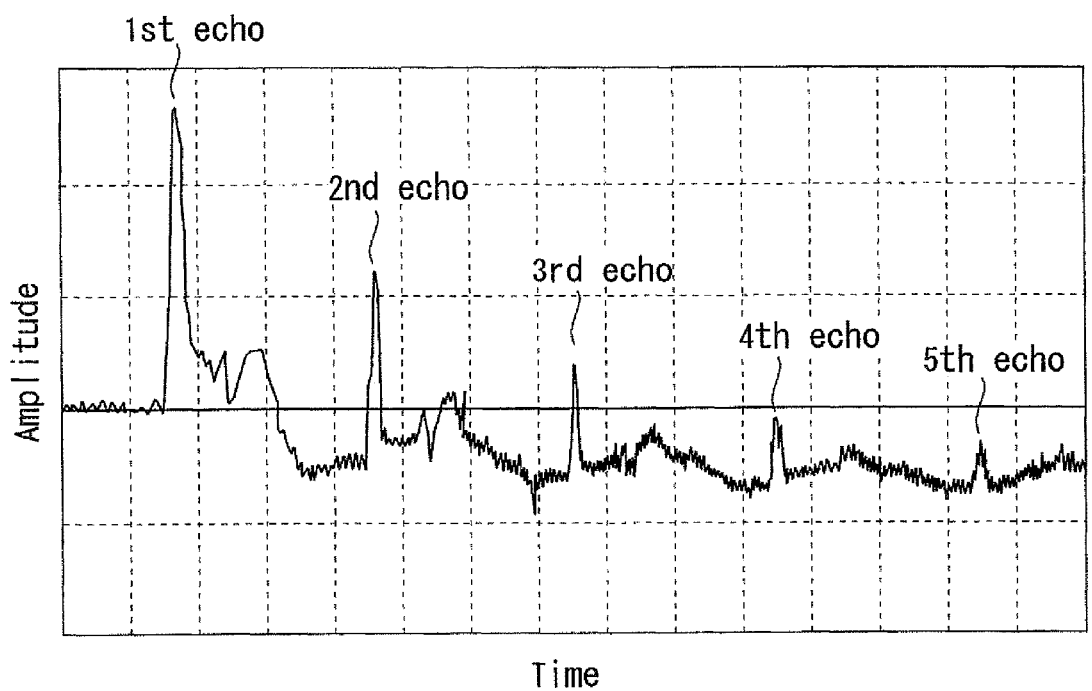
FIG. 3 is a chart showing one example of the ultrasonic wave pulse train.

In the signal processing means 6, first, the waveform of ultrasonic waves generated as an electrical signal by the laser interferometer 3 is stored in the storage means. In the waveform stored in the storage means, an ultrasonic wave pulse train such as a first ultrasonic wave echo, a second ultrasonic wave echo, . . . is observed. FIG. 3 is a chart showing one example of the ultrasonic wave pulse train.

Next, the plurality of longitudinal wave echo signals are extracted by the longitudinal wave echo extracting means 8. A specific extracting operation is as described below.

The approximate velocity V (m/s) of the longitudinal wave is made known (for example, about 5900 m/s for a steel plate) by advance measurement etc., so that time $t_1$(s) from when the pulse laser beams generated from the laser oscillator 2 is applied to the top surface of the metal piece 1 to when the first echo is detected can be calculated by the following formula.

[Formula 5]

$$t_1 = h/V \quad (5)$$

in which, h is the thickness (m) of the metal piece 1. Also, time $t_i$ to when the second and after echoes are detected can be calculated by the following formula.

[Formula 6]

$$t_i = t_{(i-1)} + 2h/V \quad (6)$$

in which, i is the number of the echo. Therefore, the longitudinal wave echo extracting means 8 has only to cut out a waveform from time $(t_i - \Delta t)$ to time $(t_i + \Delta t)$ from the waveform stored in the storage means. The time width $\Delta t$ for determining a waveform recording range should take a value far larger than the pulse width of the pulse ultrasonic waves.

Next, in the signal processing means 6, the plurality of longitudinal wave echoes extracted by the longitudinal wave echo extracting means 8 is frequency-analyzed.

Specifically, the amount of attenuation for each frequency is calculated from the difference in spectrum intensity between longitudinal wave echo signals. Next, if necessary, a diffusion attenuation correction and a transmission loss correction are made to calculate the frequency characteristics of attenuation constant. For the frequency characteristics of attenuation constant, the coefficient vector of multi-order function is determined by fitting a multi-order function such as a quartic curve to the attenuation constant by the least-squares method etc. From the coefficient vector of multi-order function obtained when the quartic curve is fitted to the attenuation constant by the least-squares method etc. and the scattering coefficient S obtained by separately measuring a metal piece whose grain size is known for calibration, the measurement value $d_0$ of crystal grain size before a correction using the volume ratio of each substructure is made is calculated.

Specifically, the above-described processing is as described below.

The energy contained in each longitudinal wave echo is decreased gradually by the loss at the time of reflection and the attenuation caused by propagation in material. If, taking out the portions of the first echo and the second echo only, the energy (power spectrum) of each portion is determined by frequency analysis, in the second echo, the attenuation of energy in accordance with Formula (1) takes place because the propagation distance of the second echo is longer by two times of the material thickness h than that of the first echo. Also, if the amount of attenuation between both echoes is determined as a difference with the power spectrum of the first echo, the amount of attenuation is indicated by a steadily increasing curve. This curve corresponds to a value obtained by multiplying the attenuation constant a in Formula (2) by a propagation distance difference 2 h. Therefore, the coefficients in Formula (2) at the unit propagation distance are determined by the least-squares method etc. From the scattering constant S having been determined in advance by the standard sample and $a_4$ of the coefficients determined as described above, Formula (3) is calculated backwards, by which the measurement value $d_0$ of crystal grain can be determined.

Also, the moving means 4 is made up of, for example, a mirror (not shown) arranged between the laser oscillator 2 for transmission and the metal piece 1 and an electrically movable stand (not shown) on which the mirror is provided. The moving means 4 has only to be capable of relatively changing the irradiation position on the metal piece 1 of the pulse laser beams generated from the laser oscillator 2 and the detection position on the metal piece 1 at which the pulse ultrasonic waves are detected by the laser interferometer 3, and may be configured, for example, by an electrically movable stand on which the laser oscillator 2 for transmission itself is placed, an electrically movable stand on which the laser interferometer 3 itself is placed, and the like.

Also, the control means 5 operates the moving means 4 based on the time from the transmission of pulse ultrasonic waves to the detection carried out by the laser interferometer 3 to further improve the measurement accuracy at the time when the microstructural feature and material property of the metal piece 1 are monitored. As described above, the longitudinal wave has a strong directivity, and when the laser beams are applied perpendicularly to the surface of the metal piece 1, the amplitude intensity in the direction perpendicular to the ultrasonic wave transmission surface becomes strongest. Therefore, the signal intensity detected by the laser interferometer 3 for reception becomes highest when the detection position of the laser interferometer 3 is aligned with the vertical line from the irradiation position of the pulse laser beams generated from the laser oscillator 2 for transmission, and a longitudinal waveform that is properly separable from noise and signals of other oscillation modes can be obtained. Therefore, for example, in the case where the crystal grain size of the metal piece 1 is measured, the moving means 4 is operated by the control means 5 so that the irradiation position of the pulse laser beams generated from the laser oscillator 2 and the detection position of the laser interferometer 3 are arranged as described above.

Figure 4:
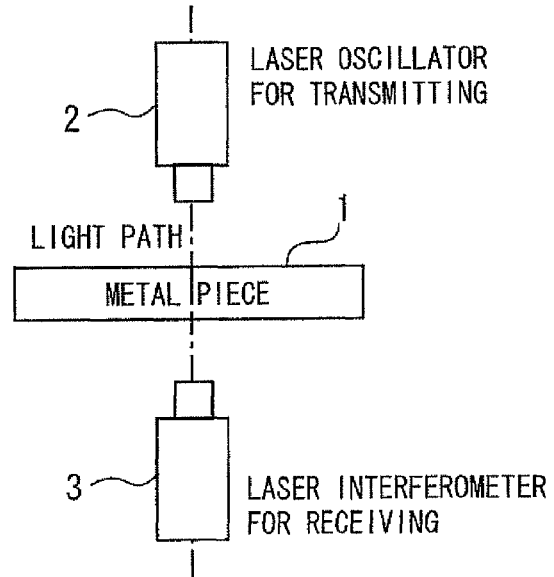
FIG. 4 is a schematic view showing the arrangement of the microstructural feature and material property monitoring device for a metallic material in accordance with a first embodiment of the present invention.
Figure 5A:
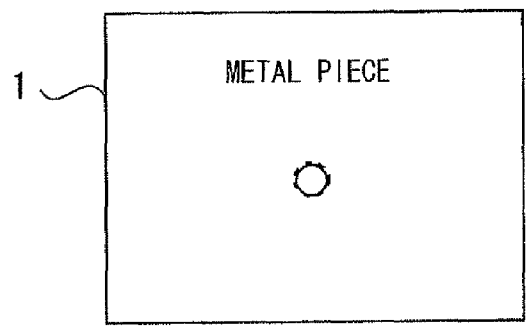
FIGS. 5a and 5b are diagrams showing the monitoring state of the microstructural feature and material property monitoring device for a metallic material shown in FIG. 4.
Figure 5B:
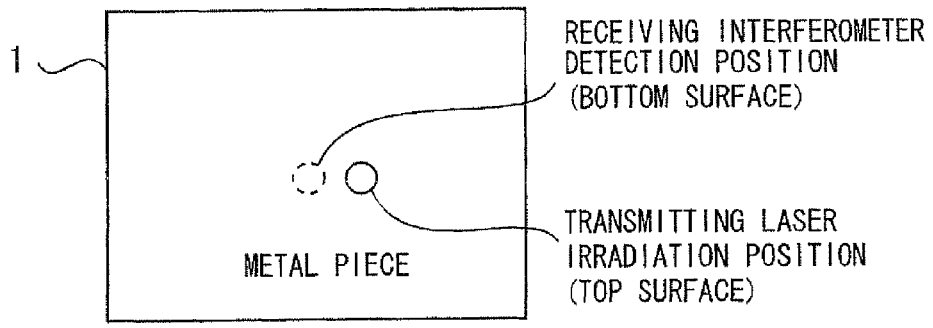

FIG. 4 is a schematic view showing the arrangement of the microstructural feature and material property monitoring device for a metallic material in accordance with the first embodiment of the present invention, and FIGS. 5a and 5b are diagrams showing the monitoring state of the microstructural feature and material property monitoring device for a metallic material shown in FIG. 4. In FIG. 4, the laser oscillator 2 for transmission and the laser interferometer 3 for reception are arranged opposedly in the up and down direction with the metal piece 1 being held therebetween. FIGS. 5a and 5b show a state in which the metal piece 1 shown in FIG. 4 is viewed from the upside. In FIGS. 5a and 5b, the solid-line circle indicates the irradiation position of the laser beams generated from the laser oscillator 2 on the top surface of the metal piece 1 (hereunder, in the explanation with reference to FIGS. 4 to 6, referred to as a "transmitting laser irradiation position"), and the broken-line circle indicates the detection position of the laser interferometer 3 on the bottom surface of the metal piece 1 (hereunder, in the explanation with reference to FIGS. 4 to 6, referred to as a "receiving interferometer detection position"). In monitoring the microstructural feature and material property of the metal piece 1 utilizing the longitudinal wave of pulse ultrasonic waves, as shown in FIG. 5a, the state in which the transmitting laser irradiation position and the receiving interferometer detection position are lapped on each other in the vertical direction is preferable. In such a case, the ultrasonic wave oscillations propagating in the metal piece 1 arrive at the receiving interferometer detection position through the shortest distance in the thickness direction of the metal piece 1, so that the waveform receiving state of the laser interferometer 3 becomes best. On the other hand, as shown in FIG. 5b, in the case where a vertical shift occurs between the transmitting laser irradiation position and the receiving interferometer detection position, the waveform received by the laser interferometer 3 becomes weak, which causes a measurement error.

To solve this problem, the moving means 4 is controlled by the control means 5 as described below so that the positional relationship between the transmitting laser irradiation position and the receiving interferometer detection position is optimal. First, the control means 5 actually measures the time from when the pulse laser beams are generated from the laser oscillator 2 to when the first echo is detected by the laser interferometer 3. The definition of the time to when the first echo is detected by the laser interferometer 3, that is, the first echo arrival time is thought of variously. For example, this time can be defined as the time before the recorded waveforms are scanned in succession from the pulse laser beam irradiation time, and the voltage level of received waveform exceeds a certain threshold value. This definition is arbitrary. For example, this time may be defined as the time before the waveform arrives at the peak of the first echo, or the time before the detected voltage reaches a predetermined ratio of the peak voltage. The position at which the first echo arrival time is shortest is the position at which the propagation distance in an object to be monitored is shortest. In such a case, the relative position between the transmitting laser irradiation position and the receiving interferometer detection position is optimal.

Figure 6A:
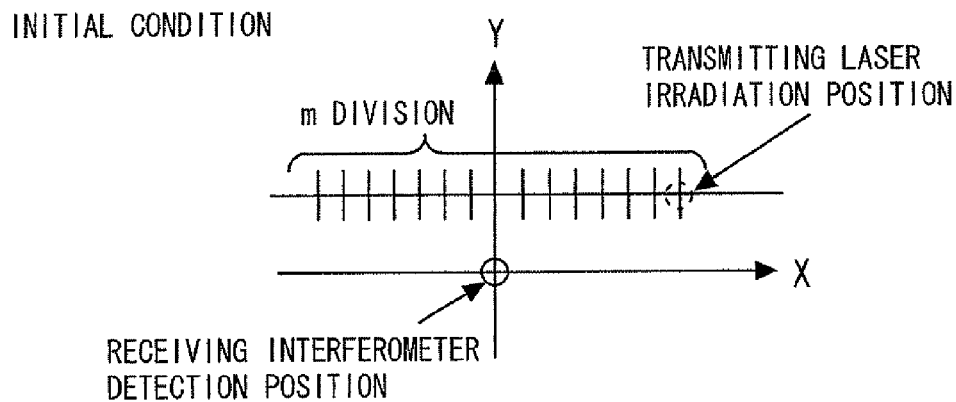
FIGS. 6a, 6b and 6c are diagrams for explaining the operation of the microstructural feature and material property monitoring device for a metallic material in accordance with a first embodiment of the present invention.
Figure 6B:
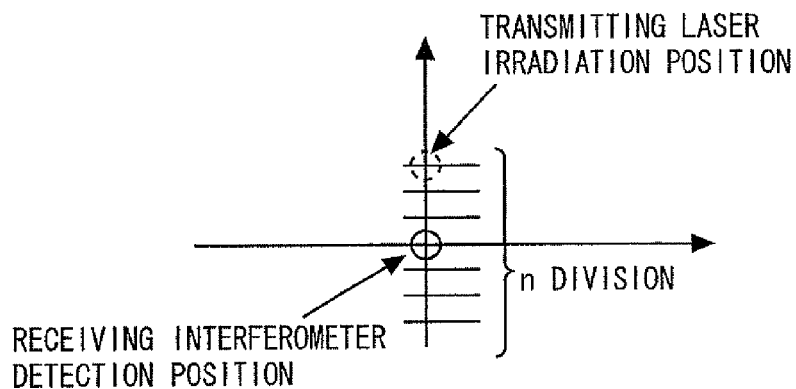
Figure 6C:
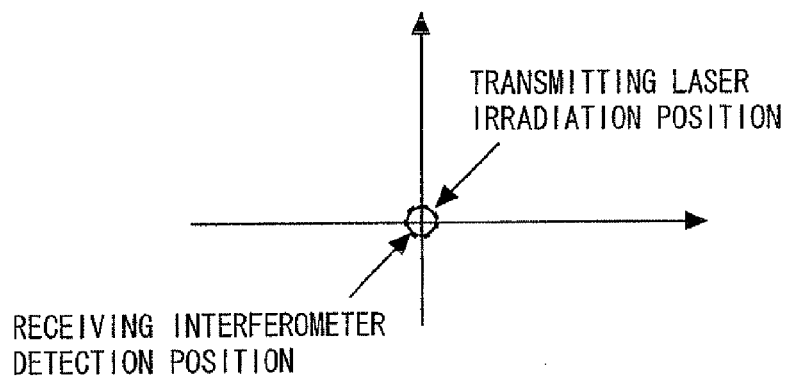
Figure 7A:
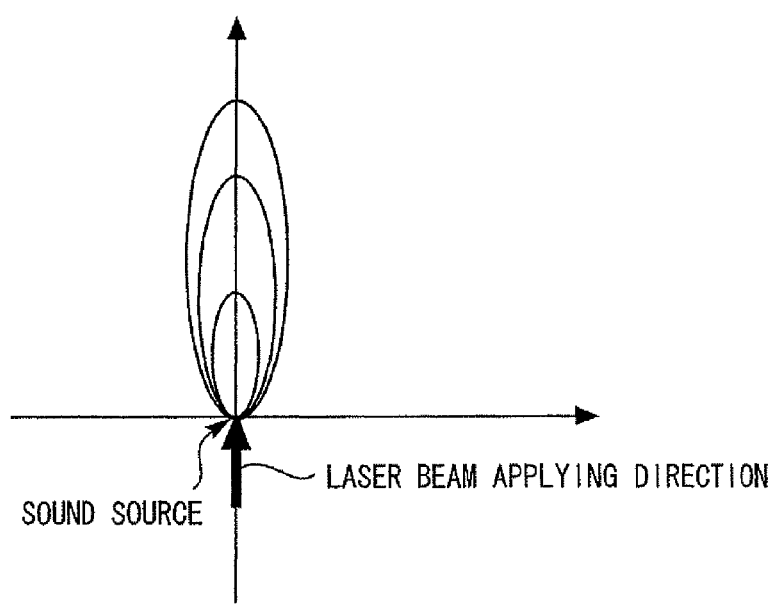
FIGS. 7a and 7b are diagrams showing the directivity of the pulse ultrasonic waves transmitted into the metal piece.
Figure 7B:
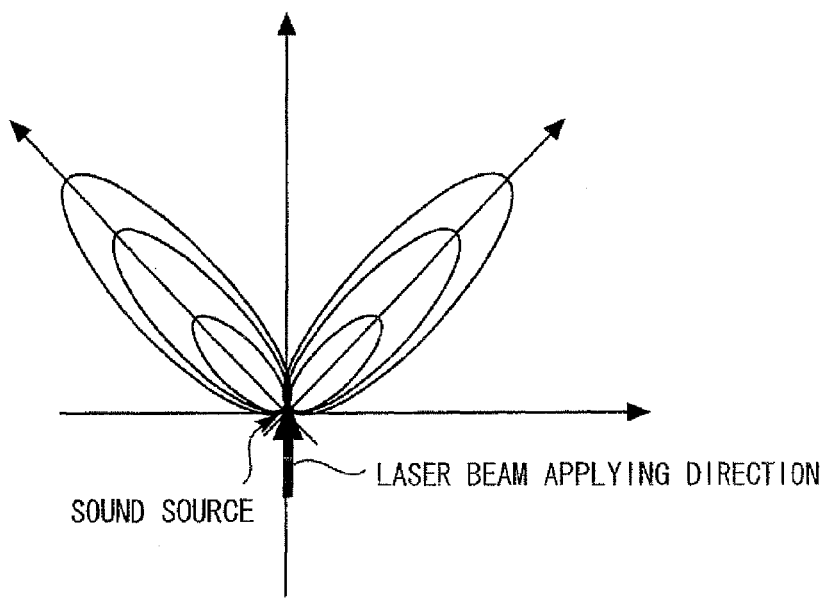

Next, the specific operation of the control means 5 for controlling the moving means 4 so that the first echo arrival time is shortest is explained with reference to FIGS. 6a, 6b and 6c. FIGS. 6a, 6b and 6c are diagrams for explaining the operation of the microstructural feature and material property monitoring device for a metallic material in accordance with the first embodiment of the present invention, and show a state in which the metal piece I shown in FIG. 4 is viewed from the downside. FIG. 6a shows an initial state in which the transmitting laser irradiation position and the receiving interferometer detection position are not aligned with each other. First, the X-axis and the Y-axis are set imaginarily with the receiving interferometer detection position being the origin. In the initial state, usually, shifts in the X-axis direction and the Y-axis direction occur between the transmitting laser irradiation position and the receiving interferometer detection position.

Then, the control means 5 first divides the X-axis into m, and takes (m+1) number of reference points in the X-axis direction. Next, the control means 5 operates the moving means 4 to move the transmitting laser irradiation position in the X-axis direction, and generates the pulse laser beams from the laser oscillator 2 at a position at which the transmitting laser irradiation position comes to each of the reference points on the X-axis. The pulse laser beams are generated from the laser oscillator 2 at each reference point and the pulse ultrasonic waves are transmitted, by which the reception waveforms at the reference points in the X-axis direction are detected by the laser interferometer 3. The signal processing means 6 analyzes the recorded reception waveforms, and detects the first echo arrival times at the reference points set in the X-axis direction. Then, the signal processing means 6 compares the detected first echo arrival times at the reference points with each other, and looks for a position at which the propagation distance in the object to be monitored on the X-axis is shortest. This point is the position at which the relative distance between the transmitting laser irradiation position and the receiving interferometer detection position is shortest in the X-axis direction.

Next, the control means 5 divides the Y-axis into n, and takes (n+1) number of reference points in the Y-axis direction as shown in FIG. 6b. The control means 5 operates the moving means 4 to move the transmitting laser irradiation position in the Y-axis direction, and generates the pulse laser beams from the laser oscillator 2 at a position at which the transmitting laser irradiation position comes to each of the reference points on the Y-axis. The pulse laser beams are generated from the laser oscillator 2 at each reference point and the pulse ultrasonic waves are transmitted, by which the reception waveforms at the reference points in the Y-axis direction are detected by the laser interferometer 3. The signal processing means 6 analyzes the recorded reception waveforms, and detects the first echo arrival times at the reference points set in the Y-axis direction. Then, the signal processing means 6 compares the detected first echo arrival times at the reference points with each other, and looks for a position at which the propagation distance in the object to be monitored on the Y-axis is shortest. This point is the position at which the relative distance between the transmitting laser irradiation position and the receiving interferometer detection position is shortest in the Y-axis direction.

By the above-described operation, the positional relationship best suitable for the reception of longitudinal wave, in which the relative distance between the transmitting laser irradiation position and the receiving interferometer detection position is shortest, can be established. FIG. 6c shows a state in which the positional relationship best suitable for the reception of longitudinal wave is established by the above-described operation. The dividing method on the X-axis and the Y-axis may be arithmetical division as described above, or may be geometrical division toward the intersection point of the X-axis and the Y-axis. Also, the monitoring method may be such that the first point and the (m÷1)-th point or the (n+1)-th point, which are both ends of the measurement points, are monitored first, and the points in the line segment whose both ends are the first point and the (m+1)-th point or the (n+1)-th point are monitored.

According to the first embodiment of the present invention, by the control of the moving means 4 carried out by the control means 5, the irradiation position of the pulse laser beams generated from the laser oscillator 2 for transmission and the detection position of the laser interferometer 3 for reception can be corrected automatically so that the optimal positional relationship for calculating the microstructural feature and material property of the metal piece 1 is established. Thereby, after the irradiation position of the laser beams generated from the laser oscillator 2 and the detection position of the laser interferometer 3 have been aligned with each other, the waveform of longitudinal wave can be acquired steadily, and the microstructural feature and material property such as crystal grain size of the metal piece 1 can be measured accurately.

Figure 8A:
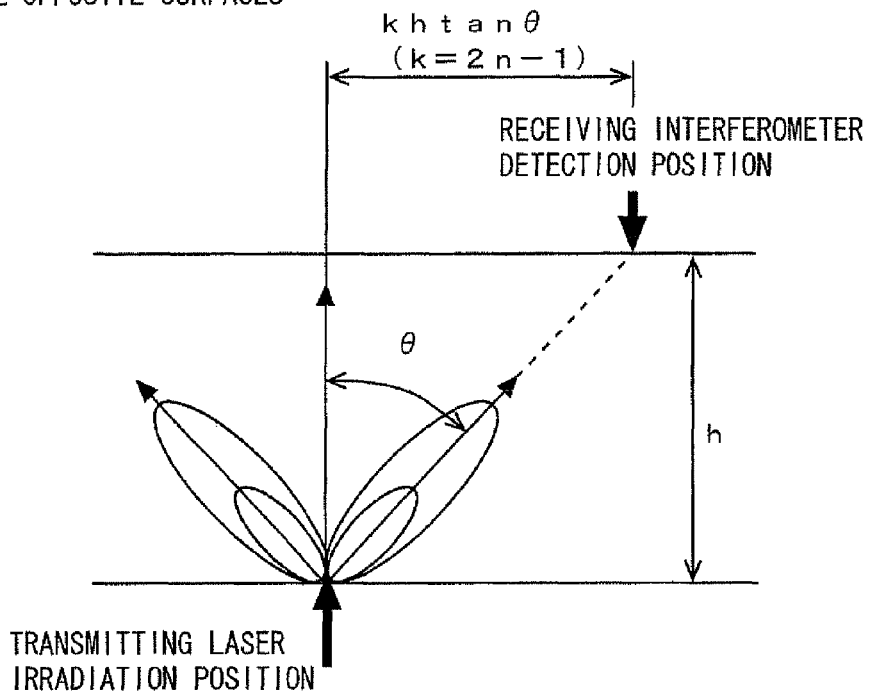
FIGS. 8a and 8b are diagrams showing another monitoring state of the microstructural feature and material property monitoring device for a metallic material in accordance with a first embodiment of the present invention.
Figure 8B:
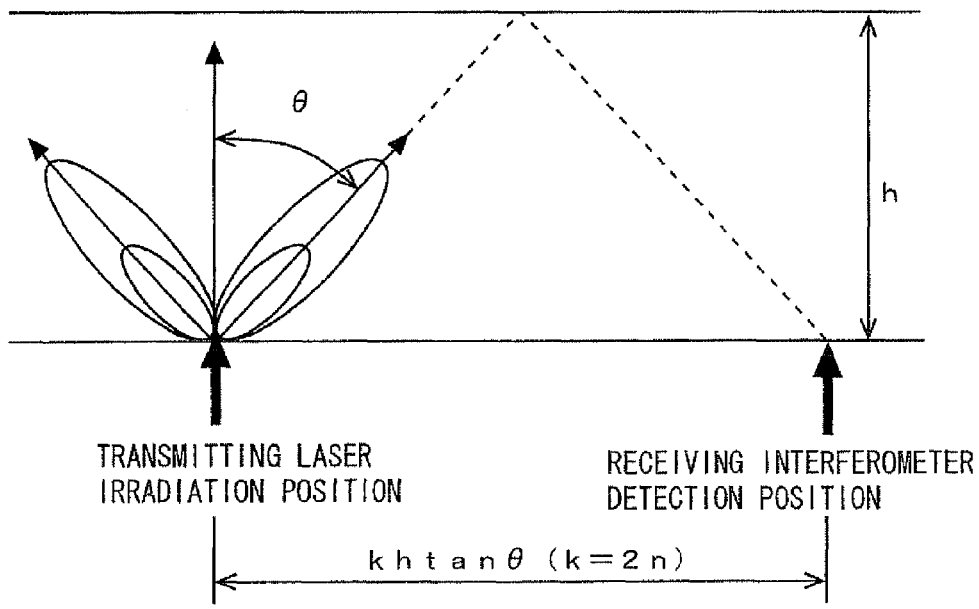

In the above explanation, the moving means 4 is controlled so that the time from the transmission of pulse ultrasonic waves to the detection carried out by the laser interferometer 3 is at a minimum, by which the crystal grain size of the metal piece I is calculated based on the waveform of longitudinal wave of pulse ultrasonic waves. On the other hand, in the case where the microstructural feature and material property such as modulus of elasticity or Lankford value are measured by detecting the waveform of another oscillation mode such as transverse wave, the operation can be performed as described below. In the control of the moving means 4, taking the angle between the irradiation direction of the laser beams generated from the laser oscillator 2 and the travel direction of the pulse ultrasonic waves of a predetermined mode as $\theta$, the control means 5 relatively moves the detection position of the laser interferometer 3 through a distance (k×h×tan $\theta$) along the bottom surface of the metal piece 1 with respect to the irradiation position of the laser beams generated from the laser oscillator 2 with the position at which the time from the transmission of pulse ultrasonic waves to the detection carried out by the laser interferometer 3 is at a minimum being a reference, in which k is an integer determined by the number n of the detected echo. For example, as shown in FIG. 8a, in the case where the transmission surface and the reception surface are opposite surfaces such as the top and bottom surfaces, the integer k is expressed as k=2n−1. Specifically, in the case where the first echo is detected, n is equal to 1, so that k=2×1−1=1. On the other hand, as shown in FIG. 8b, in the case where the transmission surface and the reception surface are the same surface, the integer k is expressed as k=2n. Specifically, in the case where the second echo is detected, n is equal to 2, so that k=2×2=4. By the above-described control, the best waveform of transverse wave of pulse ultrasonic waves can be obtained.

Also, in the first embodiment, the microstructural feature and material property monitoring device is configured so that the laser oscillator 2 for transmission is arranged above the metal piece 1 to apply pulse laser beams to the metal piece 1 from the upside, and the displacement of ultrasonic waves is detected by the laser interferometer 3 for reception that is arranged below the metal piece 1. However, the vertical arrangement of the laser oscillator 2 and the laser interferometer 3 may be reversed. Also, even if the laser oscillator 2 and the laser interferometer 3 are arranged on either one side of the metal piece 1, no problem arises. The arrangement can be selected optionally according to the conditions of environment in which the device is installed.

INDUSTRIAL APPLICABILITY

As described above, according to the microstructural feature and material property monitoring device for a metallic material in accordance with the present invention, the relative position between the irradiation position of the laser beams applied to the metallic material to propagate pulse ultrasonic waves into the metallic material and the detection position of the laser interferometer can be adjusted easily, so that the microstructural feature and material property of the metallic material can be monitored accurately.

The present invention is not limited to the configuration of the above-described embodiment. At the stage at which the present invention is carried out, the elements can be deformingly embodied within the scope in which the gist of the present invention is not changed. Also, by optionally combining the plurality of elements disclosed in the above-described embodiment, various inventions can be formed. For example, from all of the elements shown in the embodiment, some elements may be omitted. Further, a different element may be combined optionally.

The invention claimed is:

1. A microstructural feature and material property monitoring device for a metallic material, which monitors the microstructural feature and material property of the metallic material, comprising:

a laser oscillator which applies a laser beam to a first surface of the metallic material and induces pulsed ultrasonic waves in and that propagate in the metallic material;

a laser interferometer which detects the pulsed ultrasonic waves that have propagated in the metallic material on a second surface of the metallic material, on a side opposite to the first surface of the metallic material, and transmits the pulsed ultrasonic waves as an electrical signal;

moving means for relatively moving irradiation position of the laser beam generated by the laser oscillator and detection position of the laser interferometer;

control means which aligns the irradiation position of the laser beam generated from the laser oscillator and the detection position of the laser interferometer with a relative position, according to the microstructural feature and material property of the metallic material to be monitored, by controlling the moving means based on time from induction of the pulsed ultrasonic waves until detection by the laser interferometer; and calculating means which calculates the microstructural feature and material property of the metallic material based on waveform of the pulsed ultrasonic waves detected as an electrical signal by the laser interferometer.

2. The microstructural feature and material property monitoring device for a metallic material according to claim 1, wherein the control means controls the moving means so that the time from the induction of the pulsed ultrasonic waves to the detection by the laser interferometer is minimized.

3. The microstructural feature and material property monitoring device for a metallic material according to claim 2, wherein the calculating means calculates crystal grain size of the metallic material based on the waveform of the pulsed ultrasonic waves detected as an electrical signal by the laser interferometer.

4. The microstructural feature and material property monitoring device for a metallic material according to claim 1, wherein, taking plate thickness of the metallic material as h and angle between irradiation direction of the laser beam generated from the laser oscillator and travel direction of the pulsed ultrasonic waves of a predetermined mode as $\theta$, the control means relatively moves the detection position of the laser interferometer by a predetermined integer multiple of distance htan $\theta$, along the second surface of the metallic material, with respect to the irradiation position of the laser beams generated from the laser oscillator, with the position at which the time from the induction of the pulse ultrasonic waves to the detection the laser interferometer is at a minimum as a reference.

5. The microstructural feature and material property monitoring device for a metallic material according to claim 4, wherein the calculating means calculates at least one of elasticity constant and Lankford value of the metallic material based on the waveform of the pulsed ultrasonic waves detected as an electrical signal by the laser interferometer.

* * * * *